(12) United States Patent
Choi et al.

(10) Patent No.: US 9,421,282 B2
(45) Date of Patent: Aug. 23, 2016

(54) METHOD OF PREPARING IODINE SEED FOR TREATING EYE DISEASE OR CANCER, AND IODINE SEED PREPARED THEREBY

(71) Applicants: Kang Hyuk Choi, Daejeon (KR); Kwang Jae Son, Sejong (KR); Jin-Hee Lee, Daejeon (KR); Sung-Soo Nam, Daejeon (KR); Sun Ju Choi, Daejeon (KR)

(72) Inventors: Kang Hyuk Choi, Daejeon (KR); Kwang Jae Son, Sejong (KR); Jin-Hee Lee, Daejeon (KR); Sung-Soo Nam, Daejeon (KR); Sun Ju Choi, Daejeon (KR)

(73) Assignee: Korea Atomic Energy Research Institute, Daejeong (KR)

( * ) Notice: Subject to any disclaimer, the term of this patent is extended or adjusted under 35 U.S.C. 154(b) by 122 days.

(21) Appl. No.: 13/765,072

(22) Filed: Feb. 12, 2013

(65) Prior Publication Data

US 2013/0302244 A1  Nov. 14, 2013

(30) Foreign Application Priority Data

May 10, 2012  (KR) .................. 10-2012-0049643

(51) Int. Cl.
| | |
|---|---|
| *A61M 36/14* | (2006.01) |
| *A61K 51/00* | (2006.01) |
| *A61K 51/02* | (2006.01) |
| *A61K 51/12* | (2006.01) |

(52) U.S. Cl.
CPC ............... *A61K 51/00* (2013.01); *A61K 51/02* (2013.01); *A61K 51/1282* (2013.01)

(58) Field of Classification Search
CPC ..................................................... A61K 51/00
See application file for complete search history.

(56) References Cited

U.S. PATENT DOCUMENTS

| | | | |
|---|---|---|---|
| 4,323,055 A | 4/1982 | Kubiatowicz | |
| 6,485,406 B1 | 11/2002 | Ziegler et al. | |
| 2010/0155330 A1* | 6/2010 | Burba et al. ................ | 210/638 |
| 2010/0258448 A1 | 10/2010 | Whitehead et al. | |

FOREIGN PATENT DOCUMENTS

| | | |
|---|---|---|
| CN | 1307907 A | 8/2001 |
| JP | 2000-171595 A | 6/2000 |
| JP | 2012-508106 A | 4/2012 |

OTHER PUBLICATIONS

Izabela Cieszykowska, et al., An Approach to the Preparation of Iodine-125 Seed-Type Sources, Nukleonika, vol. 50, pp. 17-22, 2005.
C. Mathew, et al., A Novel Approach for the Adsorption of Iodine-125 on Silver . . . , Applied Radiation and Isotopes, Vo. 57, pp. 359-367, 2002.
S.K. Saxena, et al., Studies on the Production and Quality Assurance . . . , Applied Radiation and Isotopes, vol. 64, pp. 441-447, 2006.
Chunfu Zhang, et al., Preparation of Iodine-125 Seed . . . , Journal of Radioanalytical and Nuclear Chemistry, vol. 252, No. 1, pp. 161-163, 2002.
U.J. Park, et al., The Adsorption of 125I on a Ag+ . . . , Journal of Radioanalytical and Nuclear Chemistry, vol. 277, No. 2, pp. 429-432, 2008.
H.S. Han, et al., The Absorption of Iodine-131 on a Ceramic Matrix, Journal of Radioanalytical and Nuclear Chemistry, vol. 262, No. 3, pp. 703-705, 2004.
Hyon-Soo Han, et al., Development of Production Technology of 125I Seed . . . , Journal of Labelled Compounds and Radiopharmaceuticals, vol. 50, pp. 321-322, 2007.

* cited by examiner

*Primary Examiner* — Snigdha Maewall
(74) *Attorney, Agent, or Firm* — Lucas & Mercanti LLP

(57) ABSTRACT

The present invention provides a technique for adsorbing I-125 on a support for treating cancer and a method of preparing an I-125 seed using the same. Since a method of preparing iodine according to the present invention uses an intermediate having phosphate-based, oxalate-based, or arsenate-based anions introduced thereinto, the intermediate has a substitution effect of iodine 3 to 5 times higher than that of a typically used intermediate having chlorine anions introduced thereinto. According to the substitution effect, control of a radiation dose may be possible during the manufacturing of an iodine seed and an iodine seed may be prepared within a shorter period of time. Also, since an amount of residual radioactive iodine may be decreased as a result of a large amount of adsorption, an amount of radioactive iodine (I-125) waste may be decreased, and the effect thereof may be also high environmentally.

9 Claims, 2 Drawing Sheets

Fig. 2

| Surface treatment | Picture | Surface treatment | Picture |
|---|---|---|---|
| Before washing | | After $HNO_3^-$ washing & $N_3^-$ introduction | |
| After washing | | After $HNO_3^-$ washing & $ASO_3^{2-}$ introduction | |
| After $HNO_3^-$ washing | | After $HNO_3^-$ washing & $PO_3^{2-}$ introduction | |
| After $HNO_3^-$ washing & $Cl^-$ introduction | | | |

METHOD OF PREPARING IODINE SEED FOR TREATING EYE DISEASE OR CANCER, AND IODINE SEED PREPARED THEREBY

CROSS-REFERENCES TO RELATED APPLICATION

This patent application claims the benefit of priority from Korean Patent Application No. 10-2012-0049643, filed on May 10, 2012, the contents of which are incorporated herein by reference.

BACKGROUND OF THE INVENTION

1. Field of the Invention

The present disclosure relates to method of preparing an iodine seed for treating eye disease or cancer, and an iodine seed prepared thereby.

2. Description of the Related Art

The prostate is an organ found only in men that makes a portion of semen and is an organ located below the bladder and near rectum. Prostate cancer is a malignant tumor that originates in the prostate gland, is one of the most common cancer types in males in the West, and is also the fastest growing cancer in males due to the effects of recent dietary habits in South Korea, which mostly develops in seniors over 50 years old. In developed regions such as North America and Western Europe, prostate cancer is the most common cancer accounting for about 20% of cancers among men, in which the frequency is the highest among cancers in males developed per year in the United States and prostate cancer is ranked second among causes of death due to cancer following lung cancer. With respect to South Korea, the frequency of prostate cancer also have been significantly increased in recent years as patients seeking hospitals have been increased due to an increase in life expectancy, an increase in seniors, westernization of dietary patterns, development of diagnostic techniques, and an increased awareness of prostate cancer. According to "Korea Central Cancer Registry Database" reported annually from the Korea Central Cancer Registry and Ministry of Health and Welfare, a proportion of prostate cancer incidence was 2.7% of cancers in males in 2001 and was ranked sixth at 3.0% in 2002, and since it has been most rapidly increased in recent years, it is expected that the incidence rate of prostate cancer will be further increased in the future. It is known that prostate cancer may be also developed due to hormone, dietary habits, and chemicals, in addition to a genetic predisposition.

Treatment methods of prostate cancer may include radical prostatectomy, irradiation, chemotherapy, or hormone therapy. Among these methods, radiation therapy using radiation is a method of treating cancer by using radioactive elements emitting gamma ray able to treat cancer, and the radiation therapy may be classified as external radiation therapy, in which cancer cells may be necrosed by external irradiation, and internal radiation therapy, in which a material emitting radiation, i.e., a radioactive magnetic fluid, is prepared and then introduced into the body, and a magnetic field is externally applied to allow radiation to be emitted to treat cancer.

I-125 has been generally used in the radiation therapy of prostate cancer. I-125 has a half-life of 59.4 days, and emits 27 key and 31 keV X-rays, and a 35 key gamma ray through an internal conversion process. The main application scope of I-125 is for medical use, and I-125 is used as an in vitro diagnostic reagent in radioimmunoassay and is also used as a source for treating eye disease and prostate cancer by being formed as a radioactive source in the form or a sealed source.

An I-125 seed has a structure in which I-125 is adsorbed on a silver (Ag) support (0.5 mm×3 mm) and a titanium tube (0.8 mm×4.5 mm) surrounds the silver support. The seed having the foregoing structure is directly inserted into the human body to treat cancer cells on internal tissues, and since the seed has low activity, the seed may be permanently left in biological tissues.

In relation to the iodine seed in which I-125 is adsorbed on silver support, "3M Brand I-125" commercialized by Lawrence Soft Ray Inc. has been commercially available as an actual iodine seed, and although "Best iodine-125" is commercially available from Best International, Inc., limitations in the preparation efficiency thereof have been pointed out so far.

With regard to the preparation of an iodine seed, a method of introducing an iodine by using electrochemical method (Non-Patent Literature 1), a method of adsorbing iodine after coating palladium (Pd) (Non-Patent Literatures 2 and 3), and a method of substituting iodine after forming an intermediate having chlorine anions ($Cl^-$) introduced thereinto using solubility difference (Patent Document 1 and Non-Patent Literature 4) are known to date.

However, since these methods may require complicated procedures and may have low substitution efficiency of iodine, the methods may have limitations in commercializing an iodine seed. Accordingly, during research into a method of effectively substituting I-125 onto a silver support, the present inventors confirm that phosphates, oxalates, and arsenates are effective as an intermediate for preparing an iodine seed, thereby leading to completion of the present invention.

PRIOR ART DOCUMENTS

Patent Document

U.S. Pat. No. 4,323,055

Non-Patent Literature

Izabela, C. et al., Nuklonika 50, (2005). 17.
S. K. Saxena. et al., App. Rad. Iso. 64, (2006). 441
C. Mathew. et al., App. Rad. Iso. 57, (2002). 359.
Chunfu. Z. et al., J. Rad. Nuc. Chem. 252, (2002). 161.

SUMMARY OF THE INVENTION

One object of the present invention is to provide a method of preparing an iodine seed for treating eye disease and cancer.

Another object of the present invention is to provide an iodine seed for treating eye disease and cancer having I-125 adsorbed on a surface of a support prepared through the preparation method according to the present invention.

In order to achieve the objects, the present invention provides a method of preparing an iodine seed for treating eye disease or cancer including: forming an intermediate by introducing one type of anions selected from the group consisting of phosphates, oxalates, and arsenates into a surface of a support (step 1); and substituting the anions of the intermediate of step 1 with I-125 (step 2).

The present invention also provides an iodine seed for treating eye disease or cancer prepared through the preparation method of the present invention and having I-125 adsorbed on a surface of a support.

Since a method of preparing iodine according to the present invention uses an intermediate having phosphate-based ($PO_4^{3-}$), oxalate-based ($C_2O_4^{2-}$), or arsenate-based ($AsO_4^{3-}$) anions introduced thereinto, the intermediate has a substitution effect of iodine (I-125) 3 to 5 times higher than that of a typically used intermediate having chlorine anions ($Cl^-$) introduced thereinto. According to the substitution effect, control of a radiation dose may be possible during the manufacturing of an iodine seed and an iodine seed may be prepared within a shorter period of time. Also, since an amount of residual radioactive iodine may be decreased as a result of a large amount of adsorption, an amount of radioactive iodine (I-125) waste may be decreased, and thus, the effect thereof may also be high in terms of environment.

BRIEF DESCRIPTION OF THE DRAWINGS

The above and other objects, features and other advantages of the present invention will be more clearly understood from the following detailed description taken in conjunction with the accompanying drawings, in which:

FIG. 2 is photographs illustrating surfaces of supports before and after introducing anions into the supports in the present invention.

DESCRIPTION OF THE PREFERRED EMBODIMENTS

Figure 1:
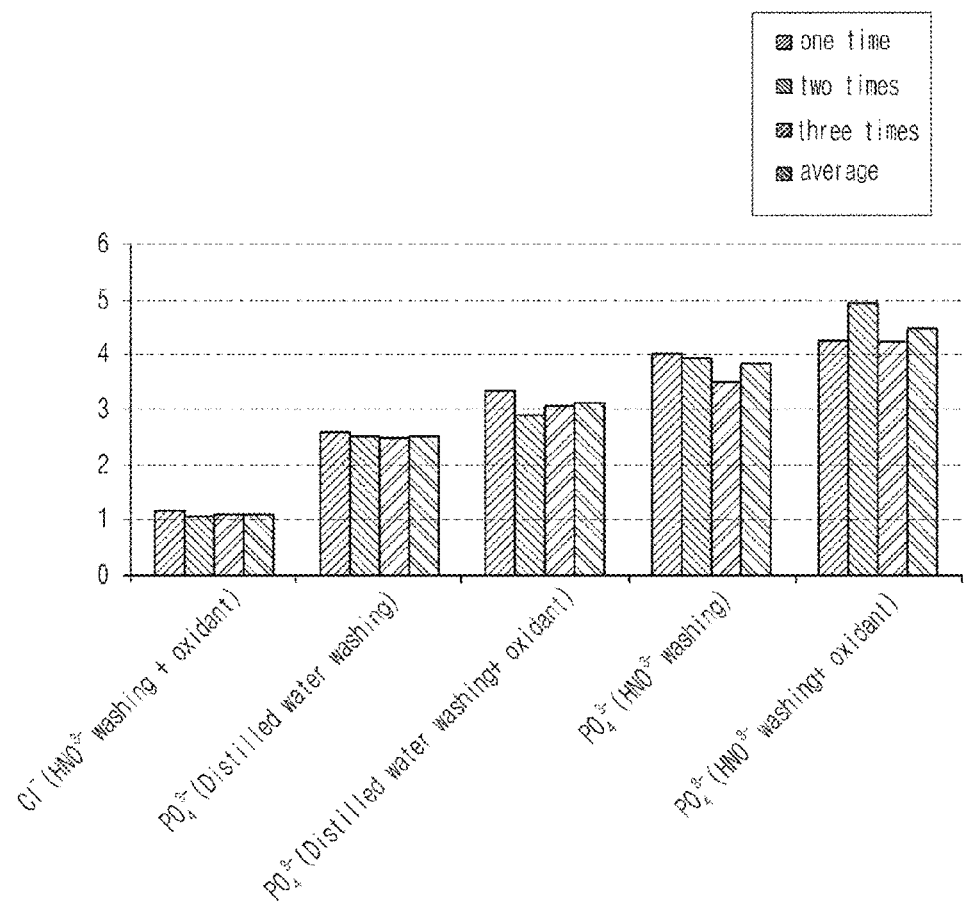
FIG. 1 is a graph illustrating the results of the number of radioactive particles in Experimental Example 1 according to the present invention.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a method of preparing an iodine seed for treating cancer including:
    forming an intermediate by introducing one type of anions selected from the group consisting of phosphates, oxalates, and arsenates into a surface of a support (step 1); and
    substituting the anions of the intermediate of step 1 with I-125 (step 2).

Hereinafter, the method of preparing an iodine seed for treating eye disease or cancer according to the present invention will be described in detail for each step.

Step 1 according to the present invention is a step of forming an intermediate, and more particularly, phosphate-based ($PO_4^{3-}$), oxalate-based ($C_2O_4^{2-}$), or arsenate-based ($AsO_4^{3-}$) anions are introduced into a surface of a support to form an intermediate.

Typically, a method of directly introducing iodine into silver by using an electrochemical method and a method of preparing an iodine seed by using an intermediate having chlorine anions ($Cl^-$) introduced thereinto are known, but the steps thereof may be complicated, or substitution efficiency may not be good. However, the method of preparing an iodine seed according to the present invention may not only have a simple process, but may also have excellent substitution yield and efficiency of iodine by preparing an intermediate having phosphate-based, oxalate-based, and arsenate-based anions introduced thereinto.

The method of substituting iodine by forming an intermediate basically is a method of using a difference between solubilities of silver iodide and the intermediate, and since typically known silver chloride has solubility higher than that of silver iodide, substitution with iodine may be facilitated. However, with respect to the intermediate having phosphate-based, oxalate-based, and arsenate-based anions introduced thereinto, substitution reactions may not only be performed by a typical solubility difference, but may also occur due to ring strain caused by the formation of the intermediate. Therefore, in the substitution reactions faster than that of a typical intermediate may occur, substitution efficiency for forming an iodine seed may be regarded as high.

In the step of forming an intermediate according to the present invention, an intermediate is prepared through a process of introducing a support into a solution, in which one type of anions selected from the group consisting of phosphates, oxalates, and arsenates is dissolved, and stirring.

The forming of the intermediate in step 1 according to the present invention may be performed after cleaning with distilled water or nitric acid, and among these, cleaning, for example, may be performed with nitric acid.

With respect to the distilled, water cleaning using distilled water, there may be an effect of removing foreign matter on the surface of the support, and with respect to the nitric acid cleaning using nitric acid, there may be an effect of etc the surface of the support and thus, a surface area may be increased.

An intermediate, in which phosphate-based anions of step 1 according to the present invention are introduced thereinto, may be prepared by using one selected from the group consisting of phosphoric acid, lithium phosphate, lithium dihydrogen phosphate, dilithium hydrogen phosphate, sodium phosphate, sodium dihydrogen phosphate, disodium hydrogen phosphate, potassium phosphate, potassium dihydrogen phosphate, dipotassium hydrogen phosphate, ammonium dihydrogen phosphate, and diammonium hydrogen phosphate. When the phosphate-based anions are introduced into a surface of silver, storage over prolonged period of time at room temperature may be facilitated and a substitution ratio of I-125 may be 4 to 5 times higher than that of a typical intermediate having chlorine anions ($Cl^-$) introduced thereinto.

Also, an intermediate, in which oxalate-based anions of step 1 according to the present invention are introduced thereinto, may be prepared by using one selected from the group consisting of lithium oxalate, sodium oxalate, potassium oxalate, ammonium oxalate, ferrous oxalate, strontium oxalate, tin oxalate, and barium oxalate. In the case that oxalic acid anions are introduced into the surface of silver, storage over prolonged period of time at room temperature may be facilitated and the substitution ratio of I-125 may be 3 to 4 times higher than that of the typical intermediate having chlorine anions ($Cl^-$) introduced thereinto.

Further, an intermediate, in which arsenate-based anions of step 1 according to the present invention are introduced thereinto, may be prepared by using one selected from the group consisting of potassium dihydrogen arsenate, sodium dihydrogen arsenate, dipotassium hydrogen arsenate, and disodium hydrogen arsenate. In the case that arsenic acid anions are introduced into the surface of silver, storage over prolonged, period of time at room temperature may be facilitated and the substitution ratio of I-125 may be 3 to 4 times higher than that of the typical intermediate having chlorine anions (Cl⁻) introduced thereinto.

Also, step 1 according to the present invention may further include treating the surface of the support with an oxidant before the formation of the intermediate.

The oxidant introduced with a compound releasing anions required to form an intermediate may be dissolved in a solution and may react with the surface of the support earlier than anions to be introduced into the support to oxidize the surface of the support, and thus, may promote the formation of the intermediate. With respect to a silver support, a surface of the support reacted with the oxidant is oxidized into silver cations (Ag$^+$) and the oxidized surface may be more easily reacted with phosphate-based, oxalate-based, or arsenate-based anions to form an intermediate.

At this time, hydrogen peroxide, manganese peroxide, sodium chromate, or potassium bichromate may be used as the oxidant.

A strong oxidant may be used as the oxidant and for example, an oxidant having a standard reduction potential of +1 volt or more may be used. Energy required for reducing a silver cation to silver is +0.8 volt, and since an oxidant having an energy greater than +0.8 volt must be used to oxidize into a silver cation, an oxidant having a standard reduction potential of +1 volt or more must be used.

Step 2 according to the present invention is a step of substituting the anions of the intermediate prepared in step 1 with I-125, and more particularly, a step of substituting the anions on the surface of the intermediate with I-125 by introducing the intermediate into an I-125 solution and stirring.

Also, step 2 according to the present invention may further include sealing with titanium (Ti) after finishing the substitution of I-125 onto the support.

An iodine seed prepared from the intermediate is inserted and installed in the inside of a titanium tube, and is then prepared through welding both ends of the tube by a laser beam irradiated within a focal length of a laser welding apparatus. The iodine seed may safely reach a position where cancer cells exist in the body by being sealed in titanium.

Further, the present invention provides an iodine seed for treating cancer prepared through the foregoing preparation method and having I-125 adsorbed on a surface of a support.

The iodine seed is inserted into internal tissue of a patient for treatment, and may not only increase therapeutic effect by removing cancer cells or preventing metastasis and proliferation of cancer cells through permanently being inserted into the patient, but may also have an excellent effect of decreasing the possibility of generating side effects.

At this time, silver (Ag), ceramic containing silver, and heavy metal surface treated with silver may be used as the support, and for example, silver may be used among these materials.

Ag, as an X-ray marker, may be identified by the insertion position thereof in in vivo tissues and has an excellent adsorption rate with respect to I-125, and thus, may be usefully employed.

The cancer treated by the iodine seed according to the present invention is prostate cancer and the present invention is not limited thereto.

Hereinafter, the present invention will be described in detail according to preparation examples and examples.

However, the following preparation examples and examples are provided for illustrative purposes only, and the scope of the present invention should not be limited thereto in any manner.

Preparation Example 1

Preparation of I-125 Solution

An iodine solution related to I-125 adsorption was prepared by using sodium iodide (NaI), a stable isotope as a carrier. Iodine corresponding to 2000 mCi of the I-125 solution was dissolved in a 0.01 N NaOH solution (10 ml) to prepare an I-125 solution. Solutions actually used in experiments were prepared by respectively diluting 10 ml of the solution thus prepared with 100 mCi/0.5 ml, 50 mCi/0.5 ml, and 20 mCi/0.5 ml and used during the preparation of iodine seeds. In the case of preparing seeds for the experiments, 0.5 mCi/0.05 ml of I-131 corresponding to a trace amount was added to each diluted solution.

Example 1

Preparation (1a) of I-125 Seeds by Using Intermediates Having Phosphate-Based Anions Introduced Thereinto Step 1: Preparation of Intermediates Having Phosphate-Based Anions Introduced Thereinto A 99% pure silver (Ag) wire having a diameter of 0.52 mm was cut into the form of a 3 mm long bar to prepare each support. 200 silver supports thus prepared were added to a vial with 30 ml of distilled water and cleaned by using an ultrasonic cleaner at room temperature for about 3 minutes, and distilled water was then removed and the Ag supports were cleaned once by adding ethanol. Cleaning was repeated twice by using the same method as the above and then terminated. 0.68 g of sodium phosphate was dissolved in distilled water to prepare 10 ml of a 0.417 M solution and 10 silver supports previously cleaned were added thereto and stirred at 200 rpm for 62 hours. After the stirring, the Ag supports were cleaned twice respectively with distilled water and acetone, and dried to prepare intermediates having phosphate-based anions introduced thereinto.

Step 2: Preparation of I-125 Seeds by Using Intermediates Having Phosphate-Based Anions Introduced Thereinto The intermediates having phosphate-based anions introduced thereinto prepared in Step 1 were added into a 50 mCi/0.5 ml of the I-125 solution prepared in Preparation Example 1 and stirring was performed at 200 rpm for 24 hours. After the stirring, the Ag supports were filtered and cleaned with distilled water, and dried to prepare I-125 seeds using intermediates having phosphate-based anions introduced thereinto.

Example 2

Preparation (1b) of I-125 Seeds by Using Oxalate-Based Intermediates

I-125 seeds using intermediates having oxalate-based anions introduced thereinto were prepared in the same manner as Example 1 except that sodium oxalate (0.56 g) was used instead of sodium phosphate (0.68 g).

Example 3

Preparation (1c) of I-125 Seeds by Using Arsenate-Based Intermediates

I-125 seeds using intermediates having arsenate-based anions introduced thereinto were prepared in the same manner as Example 1 except that sodium arsenate (1.30 g) was used instead of sodium phosphate (0.68 g).

Example 4

Preparation (2a) of I-125 Seeds by Using Intermediates Having Phosphate-Based Anions Introduced Thereinto I-125 seeds using intermediates having phosphate-based anions introduced thereinto were prepared in the same manner as Example 1 except that 30% hydrogen peroxide (50 µl) was further added during the preparation of the intermediates.

Example 5

Preparation (2b) of I-125 Seeds by Using Intermediates Having Oxalate-Based Anions Introduced Thereinto I-125 seeds using intermediates having oxalate-based anions introduced thereinto were prepared in the same manner as Example 1 except that sodium oxalate (0.56 g) was used instead of sodium phosphate (0.68 g) and 30% hydrogen peroxide (50 µl) was further added during the preparation of the intermediates.

Example 6

Preparation (2c) of I-125 Seeds by Using Intermediates Having Arsenate-Based Anions Introduced Thereinto I-125 seeds using intermediates having arsenate-based anions introduced thereinto were prepared in the same manner as Example 1 except that sodium arsenate (1.30 g) was used instead of sodium phosphate (0.68 g) and 30% hydrogen peroxide (50 µl) was further added during the preparation of the intermediates.

Example 7

Preparation (3a) of I-125 Seeds by Using Intermediates Having Phosphate-Based Anions Introduced Thereinto Step 1: Preparation of Intermediates Having Phosphate-Based Anions Introduced Thereinto A 99% pure silver (Ag) wire having a diameter of 0.52 mm was cut into the form of a 3 mm long bar to prepare each support. 200 silver supports thus prepared were added to an Erlenmeyer flask with 3M nitric acid and stirred in a water bath at 70° C. to perform a surface reaction. The surface reaction may be confirmed through changes in the surfaces of the supports to white color as gas begins to be produced. Such phenomenon is due to the fact that the surfaces thereof are converted into the form of silver oxide ($Ag_2O$) or silver nitrate ($AgNO_3$). The silver supports with etched surfaces were put into 30 ml of distilled water and cleaned by using an ultrasonic cleaner at room temperature for about 1 minute, and distilled water was then removed and the silver supports were cleaned once by adding ethanol. Cleaning was repeated twice by using the same method as the above and then terminated. 0.68 g of sodium phosphate was dissolved in distilled water to prepare 10 ml of a 0.417 M solution and 10 silver supports previously cleaned were added thereto and stirred at 200 rpm for 62 hours. After the stirring, the Ag supports were cleaned twice respectively with distilled water and acetone, and dried to prepare intermediates having phosphate-based anions introduced thereinto.

Step 2: Preparation of I-125 Seeds Using Intermediates Having Phosphate-Based Anions Introduced Thereinto The intermediates having phosphate-based anions introduced thereinto prepared in Step 1 were added into a 50 mCi/0.5 ml of the I-125 solution prepared in Preparation Example 1 and stirring was performed at 200 rpm for 24 hours. After the stirring, the Ag supports were filtered and cleaned with distilled water, and dried to prepare I-125 seeds using intermediates having phosphate-based anions introduced thereinto.

Example 8

Preparation (3b) of I-125 Seeds by Using Intermediates Having Oxalate-Based Anions Introduced Thereinto I-125 seeds using intermediates having oxalate-based anions introduced thereinto were prepared in the same manner as Example 7 except that sodium oxalate (0.56 g) was used instead of sodium phosphate (0.68 g).

Example 9

Preparation (3c) of I-125 Seeds by Using Intermediates Having Arsenate-Based Anions Introduced Thereinto I-125 seeds using intermediates having arsenate-based anions introduced thereinto were prepared in the same manner as Example 7 except that sodium arsenate (1.30 g) was used instead of sodium phosphate (0.68 g).

Example 10

Preparation (4a) of I-125 Seeds by Using Intermediates Having Phosphate-Based Anions Introduced Thereinto I-125 seeds using intermediates having phosphate-based anions introduced thereinto were prepared in the same manner as Example 7 except that 30% hydrogen peroxide (50 µl) was further added during the preparation of the intermediates.

Example 11

Preparation (4b) of I-125 Seeds by Using Intermediates Having Oxalate-Based Anions Introduced Thereinto I-125 seeds using intermediates having oxalate-based anions introduced thereinto were prepared in the same manner as Example 7 except that sodium oxalate (0.56 g) was used instead of sodium phosphate (0.68 g) and 30% hydrogen peroxide (50 μl) was further added during the preparation of the intermediates.

Example 12

Preparation (4c) of I-125 Seeds by Using Intermediates Having Arsenate-Based Anions Introduced Thereinto I-125 seeds using intermediates having arsenate-based anions introduced thereinto were prepared in the same manner as Example 7 except that sodium arsenate (1.30 g) was used instead of sodium phosphate (0.68 g) and 30% hydrogen peroxide (50 μl) was further added during the preparation of the intermediates.

Comparative Example 1

Preparation (1d) of I-125 Seeds by Using Intermediates Having Carbonate-Based Anions Introduced Thereinto I-125 seeds using intermediates having carbonate-based anions introduced thereinto were prepared in the same manner as Example 1 except that sodium carbonate (0.44 g) was used instead of sodium phosphate (0.68 g).

Comparative Example 2

Preparation (1e) of I-125 Seeds by Using Intermediates Having Azide-Based Anions Introduced Thereinto I-125 seeds using intermediates having azide-based anions introduced thereinto were prepared in the same manner as Example 1 except that sodium azide (0.27 g) was used instead of sodium phosphate (0.68 g).

Comparative Example 3

Preparation (2d) of I-125 Seeds by Using Intermediates Having Carbonate-Based Anions Introduced Thereinto I-125 seeds using intermediates having carbonate-based anions introduced thereinto were prepared in the same manner as Example 1 except that sodium carbonate (0.44 g) was used instead of sodium phosphate (0.68 g) and 30% hydrogen peroxide (50 μl) was further added during the preparation of the intermediates.

Comparative Example 4

Preparation (2e) of I-125 Seeds by Using Intermediates Having Azide-Based Anions Introduced Thereinto I-125 seeds using intermediates having azide-based anions introduced thereinto were prepared in the same manner as Example 1 except that sodium azide (0.27 g) was used instead of sodium phosphate (0.68 g) and 30% hydrogen peroxide (50 μl) was further added during the preparation of the intermediates.

Comparative Example 5

Preparation (3d) of I-125 Seeds by Using Intermediates Having Carbonate-Based Anions Introduced Thereinto I-125 seeds using intermediates having carbonate-based anions introduced thereinto were prepared in the same manner as Example 7 except that sodium carbonate (0.44 g) was used instead of sodium phosphate (0.68 g).

Comparative Example 6

Preparation (3e) of I-125 Seeds by Using Intermediates Having Azide-Based Anions Introduced Thereinto I-125 seeds using intermediates having azide-based anions introduced thereinto were prepared in the same manner as Example 7 except that sodium azide (0.27 g) was used instead of sodium phosphate (0.68 g).

Comparative Example 7

Preparation (4d) of I-125 Seeds by Using Intermediates Having Carbonate-Based Anions Introduced Thereinto I-125 seeds using intermediates having carbonate-based anions introduced thereinto were prepared in the same manner as Example 7 except that sodium carbonate (0.44 g) was used instead of sodium phosphate (0.68 g) and 30% hydrogen peroxide (50 μl) was further added during the preparation of the intermediates.

Comparative Example 8

Preparation (4e) of I-125 Seeds by Using Intermediates Having Azide-Based Anions Introduced Thereinto I-125 seeds using intermediates having azide-based anions introduced thereinto were prepared in the same manner as Example 7 except that sodium azide (0.27 g) was used instead of sodium phosphate (0.68 g) and 30% hydrogen peroxide (50 μl) was further added during the preparation of the intermediates.

Comparative Example 9

Preparation (5d) of I-125 Seeds by Using Intermediates Having Chlorinated Anions Introduced Thereinto Step 1: Preparation of Chlorinated Intermediates A 99% pure silver (Ag) wire having a diameter of 0.52 mm was cut into the form of a 3 mm long bar to prepare each support. 200 silver supports thus prepared were added to a vial with 30 ml of distilled water and cleaned by using an ultrasonic cleaner at room temperature for about 3 minutes, and distilled water was then removed and the Ag supports were cleaned once by adding ethanol. Cleaning was repeated twice by using the same method as the above and then terminated. 1 M sodium chlorate (1 ml), an oxidant, was added to 9 ml of a 1 M HCl solution to prepare a solution having a total volume of 10 ml, and 10 silver supports previously cleaned were added thereto and stirred at 200 rpm for 62 hours. After the stirring, the Ag supports were cleaned twice respectively with distilled water and acetone, and dried to prepare intermediates having chlorinated anions introduced thereinto.

Step 2: Preparation of I-125 Seeds by Using Intermediates Having Chlorinated Anions Introduced Thereinto The intermediates having chlorinated anions introduced thereinto prepared in Step 1 were added into a 50 mCi/0.5 ml of the I-125 solution prepared in Preparation Example 1 and stirring was performed at 200 rpm for 24 hours. After the stirring, the Ag supports were filtered and cleaned with distilled water, and dried to prepare I-125 seeds using intermediates having chlorinated, anions introduced thereinto.

Comparative Example 10

Preparation (5d) of I-125 Seeds by Using Intermediates Having Chlorinated Anions Introduced Thereinto

Step 1: Preparation of Intermediates Having Chlorinated Anions Introduced Thereinto A 99% pure silver (Ag) wire having a diameter of 0.52 mm was cut into the form of a 3 mm long bar to prepare each support. 200 silver supports thus prepared were added to an Erlenmeyer flask with 3M nitric acid and stirred in a water bath at 70° C. to perform a surface reaction. The surface reaction may be confirmed through changes in the surfaces of the supports to white color as gas begins to be produced. Such phenomenon is due to the fact that the surfaces thereof are converted into the form of silver oxide ($Ag_2O$) or silver nitrate ($AgNO_3$). The silver supports with etched surfaces were put into 30 ml of distilled water and cleaned by using an ultrasonic cleaner at room temperature for about 1 minute, and distilled water was then removed and the silver supports were cleaned once by adding ethanol. Cleaning was repeated twice by using the same method as the above and then terminated. 1 M sodium chlorate (1 ml), an oxidant, was added to 9 ml of a 1 M HCl solution to prepare a solution having a total volume of 10 ml, and 10 silver supports previously cleaned were added thereto and stirred at 200 rpm for 62 hours. After the stirring, the Ag supports were cleaned twice respectively with distilled water and acetone, and dried to prepare intermediates having chlorinated anions introduced thereinto.

Step 2: Preparation of I-125 Seeds by Using Intermediates Having Chlorinated Anions Introduced Thereinto The intermediates having chlorinated anions introduced thereinto prepared in Step 1 were added into a 50 mCi/0.5 ml of the I-125 solution prepared in Preparation Example 1 and stirring was performed at 200 rpm for 24 hours. After the stirring, the Ag supports were filtered and cleaned with distilled water, and dried to prepare I-125 seeds using intermediates having chlorinated anions introduced thereinto.

Experimental Example 1

Measurements of Substitution Effects of I-125 Seeds According to Preparation Process The following experiments were conducted by using the iodine seeds of Examples 1 to 3 and Comparative Examples 1 and 2 in order to investigate substitution effects according to preparation conditions of the I-125 seeds according to the present invention.

3 of the respective I-125 seeds of Examples 1, 4, 7 and 10 prepared according to the present invention were randomly selected and 0.01 ml of each solution in the step of substituting intermediates with I-125 was collected to measure gamma ray of I-131 radionuclide for 60 seconds by using an HPGe semiconductor detector. Since gamma-ray emissions of I-131 radionuclide are observed at 284.3 keV (6%), 364.5 keV (81%), and 636.9 keV (7%), the results of the measurements at 364.5 keV (81%) having the highest emission rate were compared in the present invention, and the results thereof are presented in the following Table 1 and FIG. 1.

TABLE 1

|  | Number of radiation particles in collected solution (count) | Average number of radiation particles of seed (count) | Average radiation dose of seed (mCi) |
| --- | --- | --- | --- |
| Example 1 | 1555 | 10510 | 2.53 |
| Example 4 | 594 | 12881 | 3.10 |
| Example 7 | 525 | 15926 | 3.84 |
| Example 10 | 256 | 18597 | 4.48 |

As illustrated in Table 1 and FIG. 1, values of the average number of radiation particles and radiation dose of each seed were obtained in the increasing sequence of Example 1 cleaned with distilled water<Example 4 cleaned with distilled water and using an oxidant<Example 7 cleaned with nitric acid<Example 10 cleaned with nitric acid and using an oxidant. As a result, it may be understood that cleaning with nitric acid and use of an oxidant were effective in the preparation of intermediates.

Therefore, the method of preparing an iodine seed for treating cancer according to the present invention may increase efficiency of a preparation process of an iodine seed by promoting the generation of an intermediate essential for the preparation of the iodine seed, and thus, the method may be usefully employed in the preparation of the iodine seed for treating cancer.

Experimental Example 2

Measurements of Substitution Effects of I-125 Seeds According to Intermediate The following experiments were conducted by using the iodine seeds of Examples 10 to 12 and Comparative Examples 7, 8, and 10 in order to investigate substitution effects according to a type of the intermediates of the I-125 seeds according to the present invention.

Experiments were performed in same manner as Experimental Example 1 and the results thereof are presented in Table 2.

TABLE 2

| | Intermediate | Number of radiation particles in collected solution (count) | Average number of radiation particles of seed (count) | Average radiation dose of seed (mCi) |
|---|---|---|---|---|
| Example 10 | Phosphate | 256 | 18597 | 4.23 |
| Example 11 | Oxalate | 1374 | 10110 | 2.58 |
| Example 12 | Arsenate | 1878 | 10091 | 2.63 |
| Comparative Example 7 | Carbonate | 3620 | 2289 | 0.62 |
| Comparative Example 8 | Azide | 3102 | 3886 | 0.92 |
| Comparative Example 10 | Chloride | 2579 | 3288 | 0.74 |

As illustrated in Table 2, radiation doses of the iodine seeds prepared in Examples 10 to 12 were obtained considerably high at 4.23 mCi, 2.58 mCi, and 2.63 mCi, respectively. These values corresponded to efficiencies about 3 to 5 times higher than that of a typical iodine seed prepared by using a chloride intermediate and implied that an amount of I-125 substituted during the same period of time was large. In general, a higher substitution ratio was obtained in intermediates having solubility higher than that of silver iodide (AgI). However, as illustrated in the following Table 3, it may be understood that the intermediates according to the present invention had solubilities relatively lower than that of a typical intermediate having chlorine anions (Cl⁻) introduced thereinto. Therefore, it may be understood that I-125 substitution of the intermediate did not depend only on the solubility.

TABLE 3

| Compound | Chemical formula | Solubility ($K_{SP}$, 25° C.) |
|---|---|---|
| Silver chloride | AgCl | $1.77 \times 10^{-10}$ |
| Silver bromide | AgBr | $5.35 \times 10^{-13}$ |
| Silver iodide | AgI | $8.52 \times 10^{-17}$ |
| Silver arsenate | $Ag_3AsO_4$ | $1.03 \times 10^{-22}$ |
| Silver carbonate | $Ag_2CO_3$ | $8.46 \times 10^{-12}$ |
| Silver oxalate | $Ag_2C_2O_4$ | $5.40 \times 10^{-12}$ |
| Silver phosphate | $Ag_3PO_4$ | $8.89 \times 10^{-17}$ |

Therefore, the method of preparing an iodine seed for treating cancer according to the present invention may improve a typical substitution ratio of I-125 by using a new intermediate and thus, may be usefully employed in manufacturing iodine seeds for treating cancer.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing an iodine seed for treating eye disease or cancer, the method comprising:

introducing an anion selected from the group consisting of phosphates, oxalates, and arsenates into a surface of a support (step 1) to form an intermediate; and substituting the anion of the intermediate obtained from step 1 with I-125 (step 2) to form an iodine seed, wherein the support is made of one selected from the group consisting of silver (Ag), ceramic containing silver, and heavy metal surface treated with silver, and step 1 is performed by introducing a support into a solution, in which the anion selected from the group consisting of phosphates, oxalates, and arsenates is dissolved, and stirring to form the intermediate.

2. The method as set forth in claim 1, wherein the forming of the intermediate in step 1 is performed after cleaning the support with distilled water or nitric acid.

3. The method as set forth in claim 1, wherein the phosphate-based anions of step 1 are formed of one selected from the group consisting of phosphoric acid ($H_3PO_4$), lithium phosphate ($Li_3PO_4$), lithium dihydrogen phosphate ($LiH_2PO_4$), dilithium hydrogen phosphate ($Li_2HPO_4$), sodium phosphate ($Na_3PO_4$), sodium dihydrogen phosphate ($NaH_2PO_4$), disodium hydrogen phosphate ($Na_2HPO_4$), potassium phosphate ($K_3PO_4$), potassium dihydrogen phosphate ($KH_2PO_4$), dipotassium hydrogen phosphate ($K_2HPO_4$), ammonium dihydrogen phosphate (($NH_4$)$H_2PO_4$), and diammonium hydrogen phosphate (($NH_4$)$_2$$HPO_4$).

4. The method as set forth in claim 1, wherein the oxalate-based anions of step 1 are formed of one selected from the group consisting of lithium oxalate ($Li_2C_2O_4$), sodium oxalate ($Na_2C_2O_4$), potassium oxalate ($K_2C_2O_4$), ammonium oxalate (($NH_4$)$_2$$C_2O_4$), ferrous oxalate ($FeC_2O_4$), strontium oxalate ($SrC_2O_4$), tin oxalate ($SnC_2O_4$), and barium oxalate ($BaC_2O_4$).

5. The method as set forth in claim 1, wherein the arsenate-based anions of step 1 are formed of one selected from the group consisting of potassium dihydrogen arsenate ($KH_2AsO_4$), dipotassium hydrogen arsenate ($K_2HAsO_4$), sodium dihydrogen arsenate ($NaH_2AsO_4$), and disodium hydrogen arsenate ($Na_2HAsO_4$).

6. The method as set forth in claim 1, further comprising treating the surface of the support with an oxidant before introducing the anions into the surface of the support in step 1.

7. The method as set forth in claim 6, wherein the oxidant is one or more selected from the group consisting of hydrogen peroxide, manganese peroxide, sodium chromate, and sodium bichromate.

8. The method as set forth in claim 1, wherein the substituting of the anions of the intermediate with I-125 in step 2 is performed by introducing the intermediate in an I-125 solution and stirring.

9. The method as set forth in claim 1, further comprising sealing the prepared iodine seed with titanium (Ti).

* * * * *